United States Patent [19]

Pews et al.

[11] B 4,013,683

[45] Mar. 22, 1977

[54] PROCESS FOR MAKING β-BROMOCITRACONIC ANHYDRIDE

[75] Inventors: R. Garth Pews; Ralph A. Davis, both of Midland, Mich.

[73] Assignee: The Dow Chemical Company, Midland, Mich.

[22] Filed: June 12, 1973

[21] Appl. No.: 369,373

[44] Published under the second Trial Voluntary Protest Program on March 23, 1976 as document No. B 369,373.

[52] U.S. Cl. .......................................... 260/346.8 R
[51] Int. Cl.$^2$ ...................................... C07D 307/60
[58] Field of Search .................. 260/346.8 A, 346.8

[56] References Cited

OTHER PUBLICATIONS

Beilsteins Handbuch der Organischen Chemie, 4th Ed., vol. 17, p. 441 (system no. 2476), Verlag von Julius Springer, Berlin Germany, 1933.

*Primary Examiner*—Harry I. Moatz
*Attorney, Agent, or Firm*—Ralph M. Mellom; C. E. Rehberg

[57] ABSTRACT

The title compound is made by the direct bromination of citraconic anhydride in the vapor phase at 200°–500° C. with a contact time of less than about 20 seconds. The reactants are preferably diluted with an inert solvent, such as a halogenated hydrocarbon and/or a gaseous diluent, such as $N_2$.

9 Claims, No Drawings

PROCESS FOR MAKING β-BROMOCITRACONIC ANHYDRIDE

BACKGROUND OF THE INVENTION

β-Bromocitraconic anhydride has been made heretofore by the dehydrohalogenation and dehydration of α,β-dibromomethylsuccinic acid (Vaughn and Milton, J. Am. Chem. Soc., 73, 5497–8 (1951)) or by the dehydrohalogenation of α,β-dibromomethylsuccinic anhydride (Laurser et al., J. Med. Chem., 14, 619–21 (1971)). Vaughn and Milton point out the great ease with which citraconic anhydride isomerizes to itaconic anhydride. In the very labile acid system Itaconic ⇌ citraconic ⇌ mesaconic only about 15% of the equilibrium mixture is in the citraconic configuration (Whitmore, Organic Chemistry, D. Van Nostrand, 1937, page 472).

SUMMARY OF THE INVENTION

β-Bromocitraconic anhydride is conveniently made in high yield and conversion by the direct vapor phase bromination of citraconic anhydride at about 200°–500°C. with a reaction time of about 3–20 seconds. Preferably, an inert solvent, such as methylene bromide, is used to dilute the reactants. A gaseous diluent, such as $N_2$, may also be used.

DETAILED DESCRIPTION OF THE INVENTION

In practicing the invention, a mixture of citraconic anhydride and bromine in a molar ratio of about 1:1 to 4:1, optionally diluted with an inert solvent, is vaporized and the vapors, optionally diluted with nitrogen or other inert gas, are passed through a reaction zone maintained at a temperature of about 200°–500°C. Suitable residence times are usually about 3–20 seconds. Residence times are calculated on the basis of the volume of heated reactor space, ignoring packing, the volume of gaseous feed being corrected to reaction temperature.

The effluent from the reactor is passed through an efficient condenser and then into an HBr scrubber. Since no significant amount of brominated by-products has been observed, titration of the HBr offers an easy means of determining the extent of $Br_2$ utilization in the process.

It is usually preferred to operate with an excess of citraconic anhydride so that essentially all of the $Br_2$ is consumed in one pass. This results in the production of a mixture of β-bromocitraconic anhydride and unbrominated citraconic anhydride. This is easily separated by distillation. The preferred ratio of $Br_2$ to citraconic anhydride is about 1:1.5 to 1:2.5.

The use of an inert solvent to dissolve the reactants is preferred, though not essential. Suitable solvents include methylene bromide, bromoform, methylene chlorobromide, tribromofluoromethane and the like. The amount is not critical and will not ordinarily exceed about 5 molar equivalents, based on the citraconic anhydride. The preferred ratio is about 0.5:1 to 2.5:1.

The use of a gaseous diluent, such as $N_2$, is also noncritical, though preferred.

SPECIFIC EMBODIMENTS OF THE INVENTION

The following examples illustrate the practice of the invention.

EXAMPLE 1

A mixture of 493 g. (4.40 m) of citraconic anhydride, 370 g. (2.31 m.) of $Br_2$ and 450 g. (2.59 m.) of $CH_2Br_2$ was fed into the top of a vertical tubular reactor over a period of 19.5 hours. The reactor was a 0.75 inch by 30 inch Vycor glass tube packed with Vycor rings and heated to 375°–380°C. over a length of 24 in. A flow of $N_2$ was maintained through the reactor throughout the experiment, a total of 293 liters being used.

The effluent from the reactor was passed to a condenser, from which the uncondensed gases went to an HBr scrubber. The liquid products amounted to 1034 g. (91% of theory) while the HBr trapped by the scrubber amounted to 90% of theory. Analysis of the liquid product by NMR after stripping out the solvent showed that it consisted essentially of β-bromo- and non-brominated citraconic anhydride, no significant amount of other materials being found.

The product from several runs was combined and distilled. The β-bromocitraconic anhydride was collected at 130°–135°C. (10 mm. Hg).

Similar experiments are summarized in the table below.

| Example No. | 1 | 2 | 3 | 4 |
| --- | --- | --- | --- | --- |
| Temp. °C. | 380 | 380–390 | 375 | 375 |
| Feed: Citraconic | | | | |
| Anhydride, m. | 2.50 | 4.45 | 1.00 | 2.50 |
| $Br_2$, m. | 1.32 | 2.34 | .50 | 1.32 |
| $CH_2Br_2$, m. | 1.45 | 2.60 | .58 | 1.45 |
| $N_2$, liters | 200 | 240 | 50 | 160 |
| Residence time, sec. | 7.7 | 9.8 | 7.8 | 8.0 |
| Recovery, Organic Products, Wt., % | 85 | 100 | 90 | 89 |
| HBr, % Theor. | 100 | 83 | 100 | 100 |

We claim:
1. The process of making β-bromocitraconic anhydride by the reaction of citraconic anhydride with bromine in the vapor phase at a temperature of about 200°–500°C and with a molar ratio of citraconic anhydride to bromine of about 1:1 to about 4:1.
2. The process of claim 1 wherein the temperature is about 350°–400°C.
3. The process of claim 1 wherein the molar ratio of citraconic anhydride to bromine is about 1.5:1 to 2.5:1.
4. The process of claim 1 wherein the reactants are diluted with an inert organic diluent.
5. The process of claim 4 wherein the diluent is methylene bromide.
6. The process of claim 1 wherein the vaporized reactants are diluted with an inert gas.
7. The process of claim 1 wherein the residence time of the reactants in the reaction zone is about 3 to 20 seconds.
8. The process of claim 7 wherein the residence time is about 4 to 12 seconds.
9. The process of claim 8 wherein about 1.5 to 2.5 moles of citraconic anhydride are used per mole of bromine, the reactants are dissolved in methylene bromide, their vapors are diluted with $N_2$, the reaction temperature is about 350°–400°C. and the residence time in the reaction zone is about 4–12 seconds.

* * * * *